United States Patent [19]

Marotta, Jr. et al.

[11] Patent Number: 5,013,301

[45] Date of Patent: May 7, 1991

[54] SYRINGE HOLDER

[76] Inventors: Phillip Marotta, Jr.; Debbie Marotta; Amy L. Marotta, all of 9 Wall St., Cromwell, Conn. 06416

[21] Appl. No.: 273,243

[22] Filed: Nov. 18, 1988

[51] Int. Cl.5 ............................................. A61M 5/32
[52] U.S. Cl. .................................. 604/197; 604/198; 604/110; 604/218; 128/919
[58] Field of Search ............... 604/192, 197, 198, 263, 604/110, 136, 232; 128/919, 218

[56] References Cited

U.S. PATENT DOCUMENTS

| | | | |
|---|---|---|---|
| 2,856,924 | 10/1958 | Rockwell et al. | 604/136 |
| 2,925,083 | 2/1960 | Craig | 604/197 |
| 3,820,541 | 6/1974 | Langan | 604/187 |
| 3,973,554 | 8/1976 | Tipton | 604/187 X |
| 4,540,405 | 9/1985 | Miller et al. | 604/232 |
| 4,601,708 | 7/1986 | Jordan | 604/136 |
| 4,639,249 | 1/1987 | Larson | 604/198 |
| 4,643,724 | 2/1987 | Jobe | 604/232 |
| 4,702,739 | 10/1987 | Milorad | 604/198 |
| 4,767,413 | 8/1988 | Haber et al. | 604/198 |
| 4,787,891 | 11/1988 | Levin et al. | 604/136 |
| 4,850,973 | 7/1989 | Jordan et al. | 604/157 |
| 4,921,486 | 5/1990 | DeChellis et al. | 604/110 |
| 4,927,416 | 5/1990 | Tomkiel | 604/198 |
| 4,932,947 | 6/1990 | Cardwell | 604/198 |

FOREIGN PATENT DOCUMENTS

| | | | |
|---|---|---|---|
| 3241911 | 5/1984 | Fed. Rep. of Germany | 604/187 |
| 704152 | 4/1966 | Italy | 604/198 |
| 2141031 | 12/1984 | United Kingdom | 604/187 |

Primary Examiner—C. Fred Rosenbaum
Assistant Examiner—Mark O. Polutta
Attorney, Agent, or Firm—McCormick, Paulding & Huber

[57] ABSTRACT

A holder for a syringe to protect the user after administering an injection. The holder has a housing with an open end to receive the syringe barrel so that the needle projects beyond the other end of the housing for use. A spring retracts the needle after use, and a clip can be used to secure the syringe in its retracted position. The holder housing has means for releasably securing the syringe in a second position that provides for use of the syringe while in the holder.

8 Claims, 1 Drawing Sheet

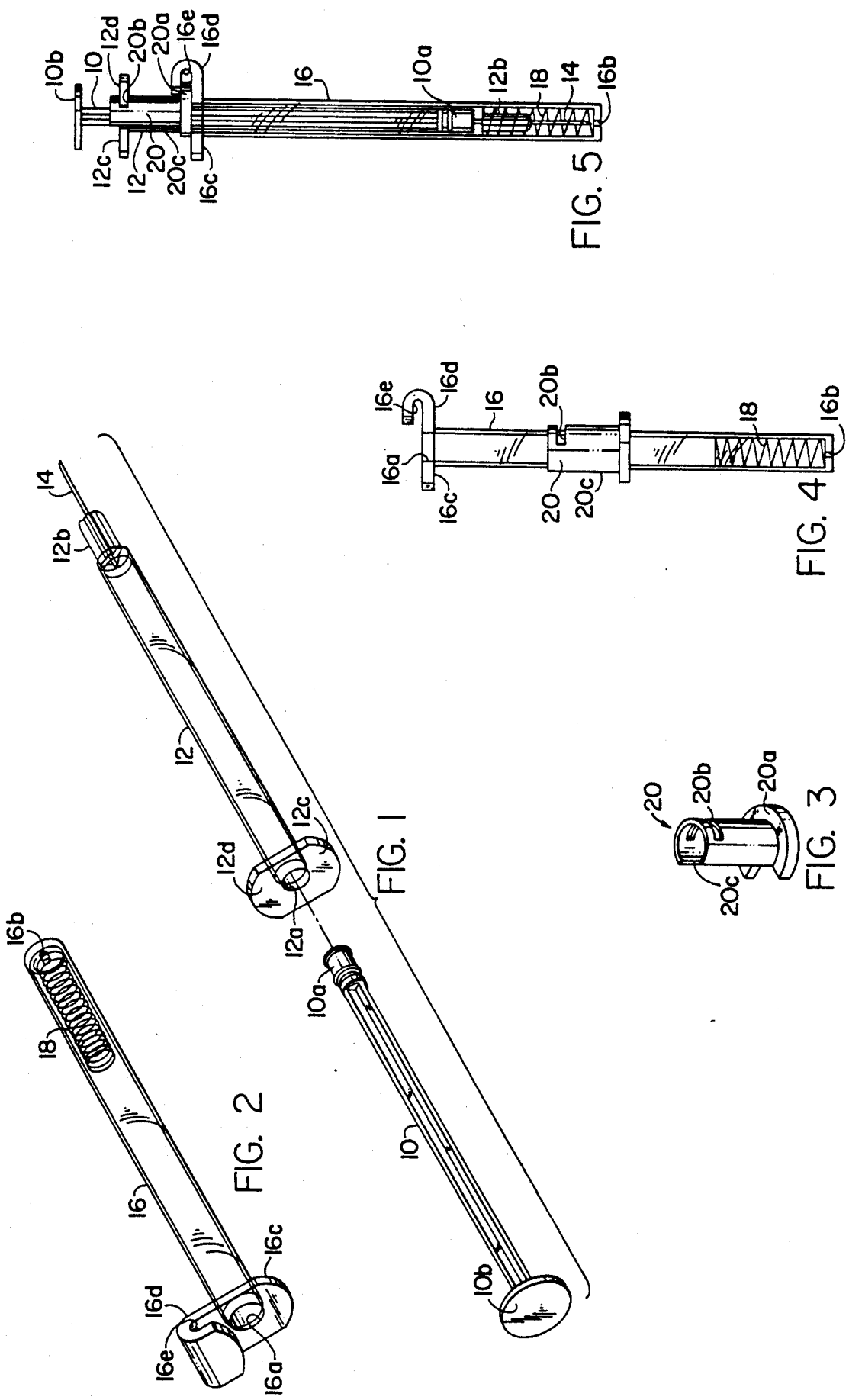

SYRINGE HOLDER

This invention relates generally to a holder for a disposable syringe, and deals more particularly with a holder that is adapted to avoid injury to the health care worker after administering an injection. The projecting needle on a conventional syringe can cause injury to the health care worker particularly after administering an injection to a patient afflicted with a communicable disease.

The general object of the present invention is to provide a syringe holder adapted to support a conventional syringe in either a retracted or a projecting position so that after an injection is administered by the health care worker the needle can be retracted into a safe position and thereby avoid injury to the health care worker and facilitate disposal of the needle and further handling by health care staff generally without danger of contamination due to accidental pricking of oneself with the used syringe.

A conventional syringe includes a plunger slidably received in a barrel, the barrel having an open end for receiving the plunger and having a needle mounted in the opposite end. The barrel further includes finger engageable projecting flanges adjacent the open end and the needle is so mounted in the opposite end as to define an annular flange surrounding the needle.

The present invention provides a syringe holder that includes a generally tubular housing having a length corresponding at least approximately to the combined length of the syringe barrel and the projecting needle. The barrel includes an internal cavity adapted to loosely receive the syringe barrel. The housing has an open end through which the syringe barrel is removably received, and the housing also has an opposite end defining a smaller opening for receiving the syringe needle. Biasing means in the form of a coiled compression spring is provided inside the housing cavity for acting on the syringe barrel to urge it and the needle toward a first position such that the needle is retracted inside the housing. A projecting flange is integrally defined by the housing adjacent the open end of the housing for cooperating with the finger engageable flanges at the open end of the syringe barrel to permit the syringe barrel to be releasably secured in the housing in a second position with the needle projecting from the housing. In this second position the health care worker can administer an injection with the conventional syringe provided inside the holder so that the protective holder is available and in a position for use by the health care worker assuring safe disposal of the used syringe.

Clip means is provided for securing the syringe barrel in this first position, where the needle is retracted for safety, and this clip means can be removably received on the housing for ready access to the health care worker once an injection has been administered and the syringe is to be secured in the holder for disposal.

BRIEF DESCRIPTION OF THE DRAWINGS

FIG. 1 shows a conventional prior art disposable syringe, the plunger being illustrated in exploded relationship to the syringe barrel.

FIG. 2 illustrates a syringe holder constructed in accordance with the present invention.

FIG. 3 illustrates a clip for securing the syringe in the syringe holder so that the needle is held in its retracted position.

FIG. 4 illustrates the clip mounted in ready position on the syringe holder, and FIG. 5 shows the syringe and holder in assembled condition with the clip securing the syringe in a position for safe disposal of both the syringe and holder.

DETAILED DESCRIPTION

Turning now to the drawings in greater detail, FIG. 1 illustrates a conventional prior art syringe, and this particular construction is presented as being representative of those syringes currently available for use by individual patients and/or for use by health care workers generally. Such a syringe comprises a plunger 10 having a piston 10a defined at one end and having a thumb engageable portion 10b at the other end. The plunger 10 is received in the open end 12a of a cylindrical barrel 12 and the diameter of the piston 10a is such that it is snugly received inside the bore of the barrel 12. The barrel further includes an opposite end defining a flange 12b surrounding the needle 14. The needle 14 is mounted in this opposite or needle end of the barrel 12, and the needle end is generally supplied by the manufacturer with a cap (not shown) that is readily removable when the syringe is to be used. The syringe is used by inserting the needle through a rubber stopper in a container filled with the appropriate medication with the plunger 10 bottomed out in the barrel 12, pulling out the plunger from the barrel causes the medication to be drawn upwardly through the needle into the space defined between the piston 10a and the needle end of the barrel.

To administer an injection the health care worker places his or her fingers under the flanges 12c and 12d provided on the barrel and place his or her thumb on the top of the plunger 10b pushing the plunger inwardly to cause the medication to be injected through the needle 14 into the patient. Once the injection has been administered the health care worker will have the responsibility to then dispose of the used syringe.

The present invention provides a holder for a syringe of the type depicted in FIG. 1 which holder facilitates disposal of the used syringe without subjecting the health care worker to the incipient dangers caused by the projecting needle 14, particularly in the situation where the needle has become contaminated by injecting medication into a patient with a communicable disease of some sort.

In accordance with the present invention the syringe holder includes a generally tubular housing 16 having an axial length corresponding generally to that of the syringe barrel, and having an internal cavity that is adapted to receive the syringe barrel 12. The housing 16 has an open end 16a through which the syringe barrel 12 is adapted to be inserted. The needle 14 at the end of the syringe barrel is adapted to be received between the convolutions of a spring biasing means 18 provided for this purpose in the end of the housing 16 opposite the one end 16a. More particularly, the barrel 16 has an opposite or needle end 16b opposite the open syringe barrel receiving end 16a and both these ends 16a and 16b are preferably sealed after fabrication following sterilization of at least the interior of the barrel 16. For example, the needle end 16b of the barrel 16 can be sealed with a material readily punctured by the needle 14 when the syringe is inserted into the holder for use.

The open end 16a of the barrel 16 can be conveniently sealed and the seal removed either by insertion of the syringe barrel 12 and needle 14 or by tearing away such a seal prior to insertion of the syringe holder into the interior of the holder housing 16.

As the syringe is inserted in the holder 16 the needle 14 moves inwardly between the convolutions of the spring 18 and the free end of the spring 18 engages the flange 12b on the syringe so as to urge the syringe outwardly of the holder 16 and more particularly so as to urge the syringe toward a first position such that the needle is retracted inside the housing. In order to provide a convenient means for securing the syringe in an active position within the holder 16 and to provide the needle 14 in a useable position projecting from the holder 16 means is defined by the housing adjacent its open end for cooperating with at least one of the finger engageable flanges 12c, 12d at the open end of the syringe barrel in order to releasably secure the syringe barrel 12 so that the needle projects beyond the housing 16. In this second or active position it will be apparent that the syringe can be used in a normal manner as described above in spite of the fact that the syringe holder 16 surrounds the syringe barrel 12.

Preferably, the means for securing the syringe barrel in this second position comprises projecting flanges 16c and 16d defined integrally with the housing and corresponding at least generally in configuration to the projecting flanges 12c and 12d on the syringe barrel 12. At least one such projecting flange, 16d in FIG. 2, is so formed as to define a radially inwardly open slot 16e for receiving one of the syringe barrel finger engageable flange portions 12c or 12d. The cylindrical syringe housing 16 permits the syringe barrel 12 to be rotatably received therein. Thus, rotating of the syringe through means approximately one fourth to one half a revolution releasably secures one flange, 12c or 12d, on the syringe barrel in the slot 16e defined for it in the syringe housing 16.

As mentioned above the syringe can be pushed against the force of spring 18 so as to cause the needle 14 to project from the end 16b of the syringe holder housing 16, and the above described means for securing the syringe to the holder can be used to hold the syringe in place in order to permit use of the device all as described above that is in a conventional fashion. Removal of the projecting finger engageable flange portion 12c or 12d from the slot 16e on the holder 16 will allow the spring 18 to retract the needle 14 back into the syringe holder housing 16. In order to secure the syringe in its retracted position means is provided for securing the syringe barrel in its retracted or first position.

FIG. 3 shows such a means as comprising a generally U-shaped clip means 20 having a flange 20a at one end adapted to be received in the slot 16e of the holder or housing 16 and having an opening or slot 20b adjacent the opposite end for receiving one of the two finger engageable flanges 12c and 12d in the syringe barrel 12. FIG. 5 shows this assembled configuration for the syringe, holder and clip. The clip 20 is fabricated from a resilient plastic material and includes an open side as indicated at 20c which open side readily permits placement of the clip 20 in position to so secure the various components in a position for disposing of the assembly without risk of injury to the health care worker and/or other members of a health facility staff in disposing of such articles generally. The slot 20c in the side of the clip 20 is readily received over the cylindrically shaped barrel 12 of the syringe for this purpose as best shown in FIG. 4. The resiliency of the clip 20 is such that this slot 20c is also adapted to be received over the exterior of the holder housing 16. The position or placement for the clip 20 as illustrated in FIG. 4 provides a convenient means for the health care worker to grasp and remove the clip 20 from this position to allow him or her to place the clip in position for holding the syringe, holder and clip in assembled relationship all as illustrated in FIG. 5.

I claim:

1. In combination with a syringe having a plunger slidably received in a barrel, and wherein the barrel has an open end and a needle end, with a finger engageable flange at the open end and an annular flange surrounding a needle in the needle end, a syringe holder comprising a generally tubular housing having a length corresponding to the combined length of the syringe barrel and needle and having an internal cavity adapted to receive the syringe barrel, said housing having an open end through which the syringe barrel is adapted to be inserted, said housing also having a needle end opposite said open end thereof, said needle end defining an opening for receiving the syringe needle, biasing means inside said housing cavity for acting on the syringe barrel to urge it and the needle toward a first position such that the needle is retracted inside the housing, means defined by said housing adjacent the open end of said housing for cooperating with the finger engageable flange at the open end of the syringe barrel to releasably secure the syringe barrel in the housing in a second position such that the needle projects from the housing, and a resilient plastic chip having an axial length corresponding generally to the axial displacement of said syringe barrel relative to said housing corresponding to said first and second positions, said clip having one portion and an opposite end portion, said one portion cooperating with said housing defined means at the open end of said housing and the opposite end portion cooperating with the finger engageable flange at the open end of said syringe barrel to secure the barrel to said housing in said first position.

2. The combination of claim 1 wherein said plastic clip is removably receivable on said housing for ready access to so secure said housing and syringe barrel after an injection.

3. The contribution of claim 1 wherein said means defined by said housing adjacent the open end of said housing for cooperating with the finger engageable flange normally defined by the syringe barrel more particularly comprises a projecting flange integrally defined by said housing and including diametrically opposed finger engageable portions similar to those normally defined by the syringe barrel, and at least one of said housing defined flange portions including an outer edge portion defining a slot for receiving one of the syringe barrel finger engageable flange portions, said housing and the syringe barrel being rotatable with respect to one another to permit said slot to releasably receive the syringe barrel flange portion.

4. The combination of claim 3 further characterized by means for securing the syringe barrel in said first position.

5. The combination comprising a syringe and a holder for said syringe, said syringe comprising a plunger, a barrel for slidably receiving said plunger, said barrel having an open end and a needle end defining an annular flange, a needle mounted in said needle end and projecting axially outwardly of said barrel, said barrel having finger engageable flanges adjacent said barrel open end, said holder comprising a generally tubular housing having a length corresponding to the combined length of the syringe barrel and needle and having an internal cavity adapted to receive the syringe barrel, said housing having an open end through which the syringe barrel is adapted to be inserted, said housing also having a needle end opposite said open end thereof, said needle end defining an opening for receiving the syringe needle, biasing means inside said housing cavity for acting on the syringe barrel to urge it and the needle toward a first position such that the needle is retracted inside the housing, means defined by said housing adjacent the open end of said housing for cooperating with the finger engageable flange at the open end of the syringe barrel to releasably secure the syringe barrel in the housing in a second position such that the needle projects from the housing, and a resilient plastic clip having an axial length corresponding generally to the axial displacement between said syringe barrel and said housing corresponding to said first and second positions, said clip having one portion and an opposite end portion, said one portion cooperating with said housing defined means at the open end of the housing and the opposite end portion cooperating with the finger engageable flange at the open end of the syringe barrel to secure the barrel to said housing in said first position.

6. The contribution of claim 5 wherein said plastic clip is removably receivable on said housing for ready access to so secure said housing and syringe barrel after an injection.

7. The contribution of claim 5 wherein said means defined by said housing adjacent the open end of said housing for cooperating with the finger engageable flange normally defined by the syringe barrel more particularly comprises a projecting flange integrally defined by said housing and including diametrically opposed finger engageable portions similar to those normally defined by the syringe barrel, and at least one of said housing defined flange portions including an outer edge portion defining a slot for receiving one of the syringe barrel finger engageable flange portions, said housing and the syringe barrel being rotatable with respect to one another to permit said slot to releasably receive the syringe barrel flange portion.

8. The combination of claim 7 wherein said resilient plastic clip has an axial length corresponding generally to the axial displacement between said first and second positions, and said clip having portions adjacent its respective ends cooperating with said housing defined means at the open end of said housing and with the finger engageable flange at the open end of the syringe barrel respectively to secure the barrel to said housing in said first position.

* * * * *